United States Patent
Enomoto et al.

(10) Patent No.: US 6,376,231 B1
(45) Date of Patent: Apr. 23, 2002

(54) SAMPLE LOADING SHEET

(75) Inventors: Tomoichi Enomoto; Hisashi Hagiwara; Kazuyoshi Kurihara; Toshio Yoshida; Yusuke Miyazaki, all of Tokyo (JP)

(73) Assignee: Hitachi Electronics Engineering Co., Ltd., Tokyo (JP)

(*) Notice: Subject to any disclaimer, the term of this patent is extended or adjusted under 35 U.S.C. 154(b) by 0 days.

(21) Appl. No.: 09/500,021

(22) Filed: Feb. 8, 2000

(30) Foreign Application Priority Data

Feb. 8, 1999 (JP) ............................ 11-030447
Jan. 28, 2000 (JP) ....................... 2000-020866

(51) Int. Cl.⁷ ........................ C12M 1/34; C12Q 1/68; C07H 21/02; B01D 57/02; G01N 15/06
(52) U.S. Cl. ................ 435/287.2; 435/287.2; 435/6; 436/94; 536/23.1; 536/24.3; 204/456; 422/68.1
(58) Field of Search ................... 435/6, 287.2; 436/94; 204/456; 422/68.1; 536/23.1, 24.3

(56) References Cited

U.S. PATENT DOCUMENTS

| | | | |
|---|---|---|---|
| 5,318,682 A | * | 6/1994 | Singer .................... 204/182.8 |
| 5,744,097 A | | 4/1998 | Machida et al. .......... 422/68.1 |
| 5,965,369 A | * | 10/1999 | Bandman et al. ............... 435/6 |

FOREIGN PATENT DOCUMENTS

| JP | 63-21556 | 1/1988 |
|---|---|---|
| JP | 11-174025 | 7/1999 |

OTHER PUBLICATIONS

Catalog of the Gel Company, 2 pages, "RapidLoad 2.0".

* cited by examiner

Primary Examiner—Bradley L. Sisson
(74) Attorney, Agent, or Firm—Mattingly, Stanger & Malur, P.C.

(57) ABSTRACT

The improved sample loading sheet for loading an assay sample in specified lane positions in a gel electrolyte layer in an electrophoresis plate to be used in a gel electrophoretic apparatus is formed of cation-exchange chromatographic paper and has part or all of at least one of its principal surfaces coated with a water-resistant resin film. The sheet enables DNA samples to be positively absorbed and migrate to produce ladder patterns at high resolution.

7 Claims, 10 Drawing Sheets

A C G T
Control

A C G T
P81

A C G T
DE81

A C G T
Filter Paper

A C G T
Glass Filter

US 6,376,231 B1

SAMPLE LOADING SHEET

BACKGROUND OF INVENTION

This invention relates to a sample loading sheet for loading an assay sample in specified lane positions in a gel electrolyte layer in an electrophoresis plate to be used in a gel electrophoretic apparatus. More particularly, the invention relates to a sample loading sheet for loading an assay sample in specified lane positions in a gel electrolyte layer in an electrophoresis plate to be used in a gel electrophoretic apparatus such as a DNA base sequencer capable of determining the base sequences of DNA by fluorescence labeling in an efficient and rapid manner.

Gel electrophoresis is practiced extensively as a technique for determining the base sequences of DNA and other proteins.

Conventionally, the sample to be subjected to electrophoresis is labelled with a radioisotope for analysis but this method has had the problem of being painstaking and time-consuming. Furthermore, the use of radioactive substances always calls for utmost safety and management and analysis cannot be performed in areas other than facilities that clear certain regulations. Under the circumstances, a method that uses fluorophores to label the sample and which detects fluorescences as emitted upon irradiation with light is being reviewed.

In this method, fluorophore-labelled DNA fragments are caused to migrate through a gel and a light excitation portion and a photodetector are provided for each electrophoresis track in an area 10–70 cm below the start point of electrophoresis. The DNA fragments are assayed as they pass through the line connecting the light excitation portion and the photodetector. A typical procedure of the method is described below. First, using as a template the DNA chain to be determined for its base sequence, DNAs of various lengths with known terminal base species are replicated by a method involving an enzymatic reaction (the dideoxy method). Then, the replicated DNAs are labelled with a fluorophore. Stated more specifically, there are prepared a group of adenine (A) fragments, a group of cytosine (C) fragments, a group of guanine (G) fragments and a group of thymine (T) fragments, all being labelled with a fluorophore. A mixture of these fragment groups is injected into separate lane grooves in an electrophoretic gel and, thereafter, a voltage is applied at opposite ends of the gel. Since DNA is a chained polymer with negative charges, it will move across the gel at a rate in inverse proportion to its molecular weight. The shorter the DNA chain (the smaller its molecular weight), the faster will it move and vice versa; this is the principle behind the fractionation of DNA by molecular weight.

Japanese Laid-Open Patent Application (kokai) No. 21556/1988 teaches a DNA base sequencer that is adapted in such a way that a line on the gel in an apparatus for electrophoresis at which laser light is applied and the direction in which photodiodes are arranged are both perpendicular to the direction in which DNA fragments migrate in the apparatus.

Figure 14:
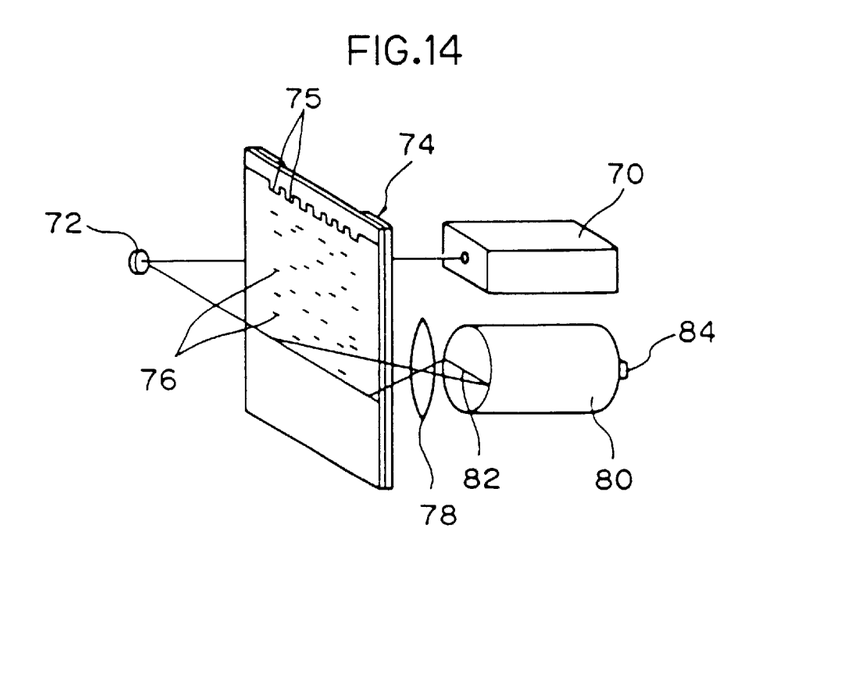
FIG. 14 shows schematically the DNA base sequencer disclosed in Japanese Laid-Open Patent Application (kokai) No. 21556/1988.

The setup of this apparatus is shown schematically in FIG. 14. In the apparatus shown in FIG. 14, a laser beam emitted from a light source 70 is reflected by a mirror 72 and launched horizontally from one side of an electrophoresis plate 74 at a predetermined point on the gel. As the fluorescence-labelled DNA fragments migrating through the gel pass through the irradiated region, they will fluoresce successively. The horizontal position of fluorescence emission tells the species of a particular terminal base, the time difference from the start of migration tells the length of a particular fragment, and the emission wavelength identifies the sample under assay. The fluorescence from each electrophoresis track is condensed by a lens 78 to focus at a light-receiving area 82 in an image intensifier 80. The received signal is amplified and converted to an electric signal in a photodiode array 84 for the purpose of various measurements. The results of measurements are processed with a computer so that the sequences of the individual DNA fragments are calculated to determine the base sequence of the DNA at issue.

Figure 15:
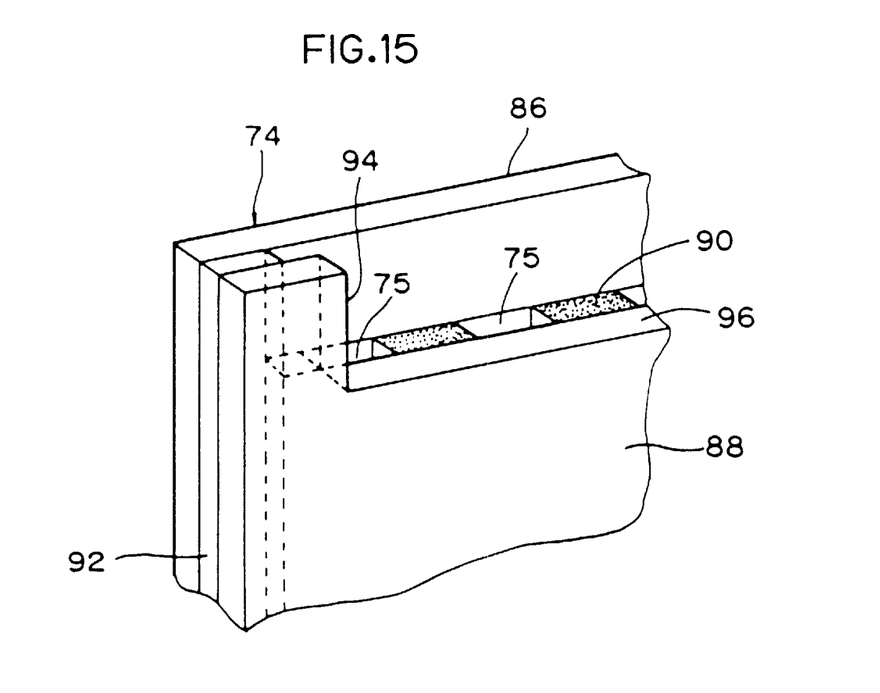
FIG. 15 is a perspective view showing partially enlarged the electrophoresis plate used in the DNA base sequencer of FIG. 14.

As shown in FIG. 15, the electrophoresis plate 74 comprises a pair of glass plates 86 and 88 between which is held a gel electrolyte layer 90 made of an electrophoresing gel (e.g. polyacrylamide gel). To regulate the thickness of the gel electrolyte layer 90, a spacer 92 is provided between the two glass plates along both vertical edges. The top edge of the glass plate 88 is cut away in a specified depth across the entire width except both lateral ends. The resulting cutout 94 provides access for a buffer solution to make contact with the top edge of gel electrolyte layer 90. The electrophoresis plate 74 has an overall thickness of about 10 mm but the thickness of the gel electrolyte layer itself is only about 0.3 mm. The upper edge of the gel electrolyte layer is comb-shaped (i.e., has indentations) and located substantially flush with the bottom 96 of the cutout 94. Fluorophore-labelled DNA fragments to be assayed are injected into grooves 75 between the teeth of the comb.

Each of the grooves 75 into which the DNA fragments are to be injected has a width of about 1.5 mm and a depth of no more than about 5 mm. Two grooves are spaced apart by a distance of about 2 mm. Such small dimensions require that a fine glass tube, such as a capillary, be used to inject the samples into the grooves 75. However, due to the transparency of the glass plates and the gel electrolyte, identifying or determining the positions of the individual grooves 75 is extremely difficult and the failure to inject the samples into the right grooves has been frequent.

Figure 16:
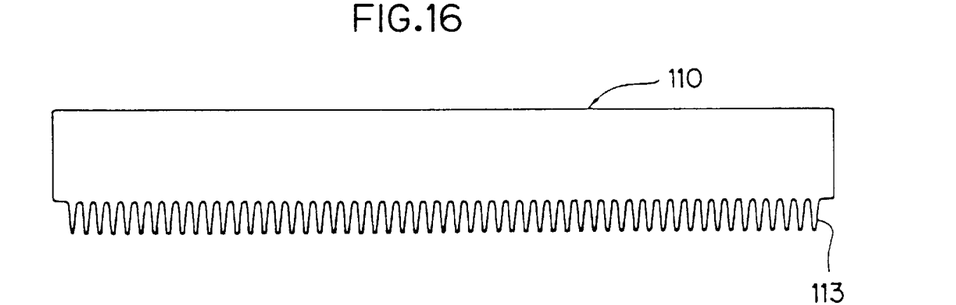
FIG. 16 is a plan view of a conventional sharktooth comb.
Figure 17:
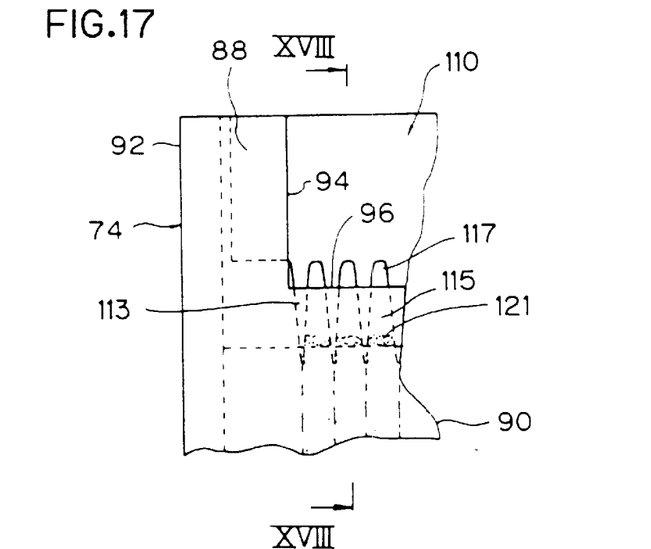
FIG. 17 is a plan view showing partially enlarged the sharktooth comb of FIG. 16 as it is inserted into the electrophoresis plate.

To support the injection of DNA samples, a sharktooth comb of the shape shown in FIG. 16 has been developed and used. The sharktooth comb is described in U.S. Pat. No. 5,744,097 which was issued to Machida et al. on Apr. 28, 1998 and herein incorporated by reference. The sharktooth comb indicated by 110 in FIG. 16 has a series of teeth 113 formed on one of its longer sides. The sharktooth comb 110 may be made of a water-swellable material such as paper. As shown in FIG. 17, the sharktooth comb 110 is inserted, usually from the top edge of the electrophoresis plate 74, into the gap between the two glass plates. The tips of the teeth 113 of the sharktooth comb 110 are slightly urged into the gel electrolyte layer. When the sharktooth comb 110 is immersed in a buffer solution, they swell and close all gaps present between the two glass plates. As a result, adjacent teeth 113 form walls that isolate two adjacent sample loading zones that are defined by spaces 115.

Figure 18:
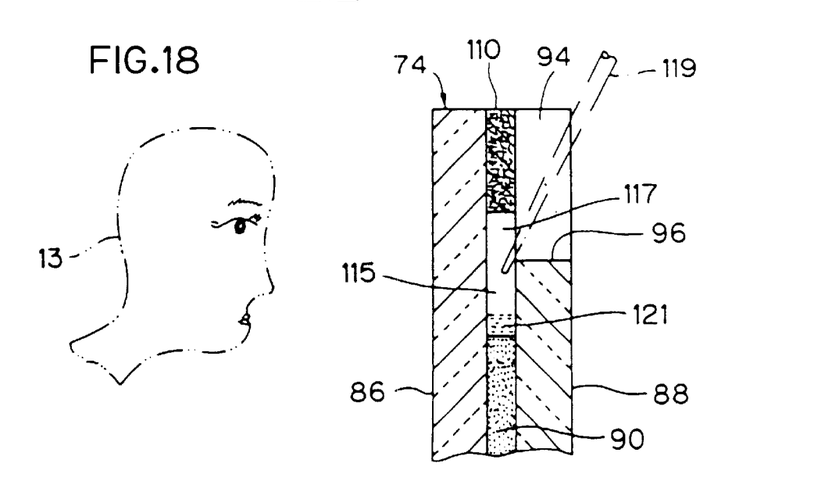
FIG. 18 is section XVIII—XVIII of FIG. 17 which is a partial diagrammatic view showing schematically how a DNA sample is injected into the top of a gel electrolyte layer.

FIG. 18 is a section taken on line XVIII—XVIII of FIG. 17. As shown, the top edge of the glass plate 88 which combines with the other glass plate 86 to form the electrophoresis plate is partly cut away in the longitudinal direction. Since the teeth 113 have a specified length, an opening 117 is formed between the root of each tooth and the bottom edge 96 of the cutout 94 in the glass plate 88. In the actual sample injecting process, the operator 13 looking through the glass plate 86 inserts the tip of a micro-injecting device 119 such as a capillary or plate chip into the sample loading space 115 via the opening 117 and injects a liquid sample 121. This process involves extreme difficulty in checking the right injecting site through the glass plate and occasionally suffers from the problem of clogging of the injection device 119. The problem of clogging can be avoided by substituting a micropipette but its use is not practically feasible since the openings 117 are very difficult to see and physically too small for the micropipette to be inserted.

To determine the base sequences of DNA, the four bases that compose the DNA, i.e., adenine (A), guanine (G), cytosine (C) and thymine (T), must be detected according to the correct order. A failure in sample injection is most likely to cause an error in the result of analysis. Hence, sample injection requires utmost care, which has been one of the reasons for the substantial drop in the operational efficiency. In particular, the failure to inject a sample into one electrophoretic track results in the need to repeat the injecting procedure over again for the whole electrophoresis plate and the mental and physical fatigue on the side of the operator who is injecting the sample is by no means negligible.

SUMMARY OF INVENTION

An object, therefore, of the present invention is to provide a sample loading sheet for use with a gel electrophoretic apparatus that substantially reduces the volume of operation of injecting DNA samples.

This object of the invention can be attained by a sampling loading sheet for loading an assay sample in specified lane positions in a gel electrolyte layer in an electrophoresis plate to be used in a gel electrophoretic apparatus, characterized in that said sheet is formed of cation-exchange chromatographic paper and has part or all of at least one principal surface thereof coated with a water-resistant resin film.

The sample loading sheet of the invention is formed of cation-exchange chromatographic paper. A DNA sample to be assayed is adsorbed by the sheet in specified positions. The sheet is then fitted in the electrophoresis plate in a gel electrophoretic apparatus and electrophoresis is performed under an applied electric voltage. Conventionally, the DNA sample was directly injected into the gel electrolyte layer in the electrophoresis plate but this cumbersome step is eliminated by using the sampling loading sheet of the invention. Although no exact mechanism has been unraveled, the following explanation may be put forward as a probable hypothesis: the cation-exchange chromatographic paper of which the sample loading sheet of the invention is formed has such low adsorbability of a fluorescence-labeled DNA sample that upon application of an electrophoretic voltage, the sample is detached from the sheet at a sufficiently high speed that the resolution is almost comparable to what is obtained by the conventional procedure of electrophoresis in which the fluorescence-labeled DNA sample is directly injected into the gel electrolyte layer.

DETAILED DESCRIPTION OF THE INVENTION

An example of the cation-exchange chromatographic paper that can be used in the invention is commercially available Whatman (registered trademark) Grade P81, which is a strong cation exchanger in the form of low-gage (ca. 0.2 mm thick) paper that essentially consists of cellulose phosphate. It has an ion-exchange capacity of $18.0\,\mu\text{Eq/cm}^2$ and adsorbs water at a rate of 125 mm/30 min. Needless to say, cation-exchange chromatographic papers other than Grade P81 can equally be used in the invention.

Figure 1:
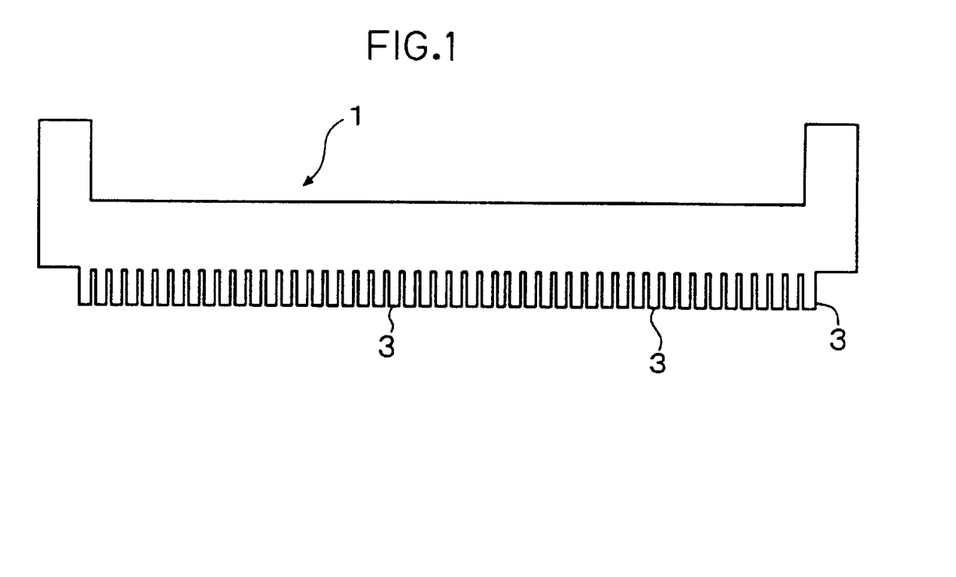
FIG. 1 is a plan view of an example of the sample loading sheet of the invention which, for use, is inserted into an electrophoresis plate in a DNA base sequencer.

FIG. 1 is a plan view of an example of the sample loading sheet of the invention. The sample loading sheet indicated by 1 has a series of teeth 3 formed on one of its longer sides. The number of teeth 3 to be formed is in no way limited and variable according to the width of the electrophoresis plate into which the sample loading sheet is to be inserted.

Figure 2:
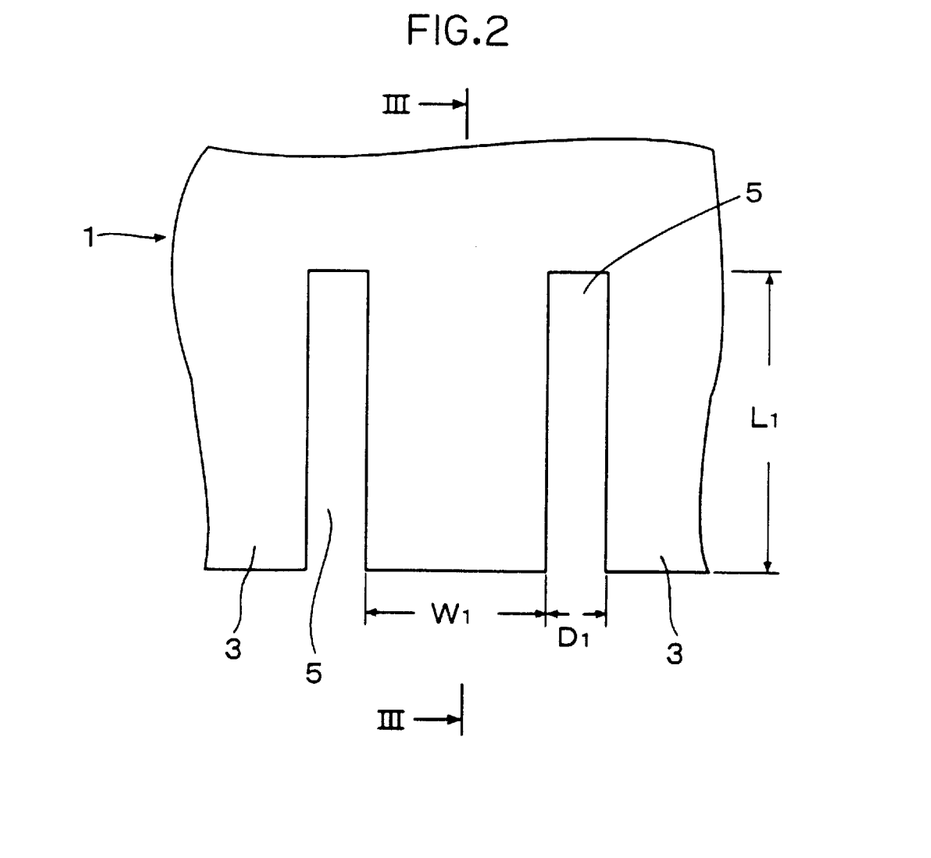
FIG. 2 is a partial enlarged plan view of a sample loading sheet having rectangular teeth.

FIG. 2 is a partial enlarged plan view of teeth 3 in the sample loading sheet of the invention. The teeth 3 are rectangular in shape but they may assume other shapes such as a trapezoid and a triangle. In the sample loading sheet of the invention, each tooth 3 defines one lane and adjacent lanes are isolated by the cutout 5 between teeth 3 so that there will be no contamination by adjacent lanes.

About 1.5–4 µl of DNA sample is to be added to each lane during electrophoresis. To adsorb this quantity of DNA sample, every tooth 3 should have an area of about 9–24 mm². For example, a tooth area of at least about 12 mm² is necessary to absorb 2 µl of DNA sample. Therefore, by referring to the amount of DNA sample to be added to each lane, one can determine the area of a tooth that is necessary to adsorb the DNA sample, which in turn is used to determine the length ($L_1$) and width ($W_1$) of each tooth 3.

To give an example, the length ($L_1$) of a tooth 3 may be in the range of 3–10 mm. If the length ($L_1$) of a tooth 3 exceeds 10 mm, it will easily bend, making it difficult to fit the sample loading sheet 1 in the electrophoresis plate. The width ($W_1$) of a tooth 3 which defines the width of a lane may be in the range of 1–10 mm. If the width ($W_1$) of a tooth 3 is less than 1 mm, not only is the sample loading operation difficult to perform but also the tooth 3 will easily bend, making it difficult to fit the sample loading sheet in the electrophoresis plate. If the width ($W_1$) of a tooth 3 exceeds 10 mm, it will not easily bend, thus facilitating the fitting of the sample loading sheet in the electrophoresis plate. On the other hand, the total number of teeth 3 that are provided across the sample loading sheet 1 and, hence, the number of DNA samples that can be assayed at a time is reduced, making it necessary to perform an increased number of assays. The distance $D_1$ between teeth 3 is not limited to any particular value if it is large enough to ensure that adjacent teeth 3 can physically be clearly distinguished and the contamination by adjacent lanes can be positively prevented during injection of DNA samples. To give an example for the case of rectangular teeth 3 that are shown in FIG. 2, the three dimensions $L_1$, $W_1$ and $D_1$ may be 6.5 mm, 2.2 mm and 0.8 mm, respectively.

The sample loading sheet 1 of the invention is essentially formed of water-adsorbing, cation-exchange chromatographic paper, as exemplified by Whatman (registered trademark) Grade P81. However, the sample loading sheet solely formed of cation-exchange chromatographic paper becomes easy to tear and difficult to handle upon adsorbing water. To deal with this situation, at least one surface of the sample loading sheet is preferably coated with a water-resistant or water-repellant film so that it will have an increased overall mechanical strength.

Figure 3:
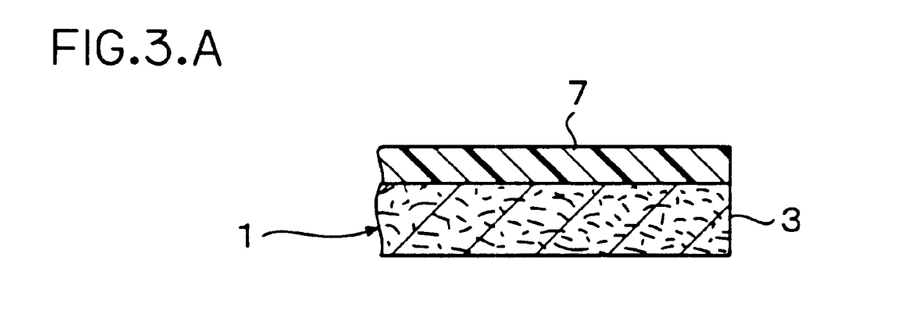
FIGS. 3A, 3B and 3C show diagrammatically three examples of section III—III of FIG. 2 having a coating formed on the sample loading sheet.

FIGS. 3A, 3B and 3C are three examples of section III—III of FIG. 2 showing diagrammatically a part of a tooth of the sample loading sheet of the invention that is formed of cation-exchange chromatographic paper and which has a coating formed on it. FIG. 3A shows an embodiment in which the coating 7 is formed on one side of the sample loading sheet 1. FIG. 3B shows an embodiment in which the coating 7 is formed on both sides of the sample loading sheet 1. FIG. 3C shows an embodiment in which the coating 7 is formed on one side of the sample loading sheet 1 except in the tip portion of the top of a tooth 3. In short, the coating 7 can be provided in part (such as a tooth or teeth) or all of at least one side of the sample loading sheet 1.

The coating 7 may be formed by applying a water-resistant or water-repellent thermoplastic resin or a hydrophobic paint (such as wax). Exemplary thermoplastic resins that can be used in the invention include polyethylene, polypropylene, other polyolefins, nylon, Teflon, poly(vinyl chloride), poly(vinylidene chloride), polybutadiene, polyacrylates, polystyrene and EVA resins. Other resins can also be used. The thickness of the coating 7 is not limited to any particular value but it is necessary that the total thickness of the cation-exchange chromatographic paper and the coating should be less than 0.3 mm. The coating 7 may be colorless and transparent or it may take on a different color than the cation-exchange chromatographic paper which typically is white.

Figure 4:
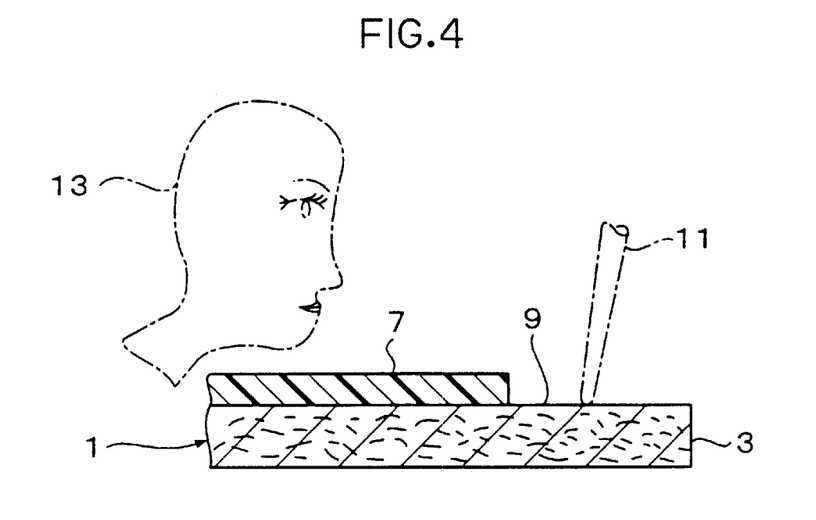
FIG. 4 shows schematically how a DNA sample is adsorbed by the exposed portion of a tooth of the sample loading sheet shown in FIG. 3C.

If the coating 7 is provided up to the most forward end of each tooth 3 as shown in FIGS. 3A and 3B, the teeth 3 of the sample loading sheet 1 may be immersed in a DNA sample so that it is adsorbed by the teeth from their uncoated (exposed) side edges (commonly called "cut edges". If the tip portion of the top of each tooth 3 is exposed as shown in FIG. 3C, the method shown in FIG. 4 may be adopted, according to which a suitable amount of DNA sample is adsorbed by the teeth via a liquid injection means 11 such as a micropipette, a micro-syringe or a capillary that is placed in contact with the exposed part 9 of the cation-exchange chromatographic paper. The preferred injection means 11 is a micropipette since it does not easily clog and can eject a constant volume of liquid at all times. Injection of a DNA sample can be performed by the operator who only need place the sample loading sheet 1 on a level bench (such as a desk or table, not shown) and watch the exposed part 9 as the DNA sample is being adsorbed by the teeth. In this way, the operational throughput is markedly improved over the conventional practice of injecting DNA samples.

Figure 5:
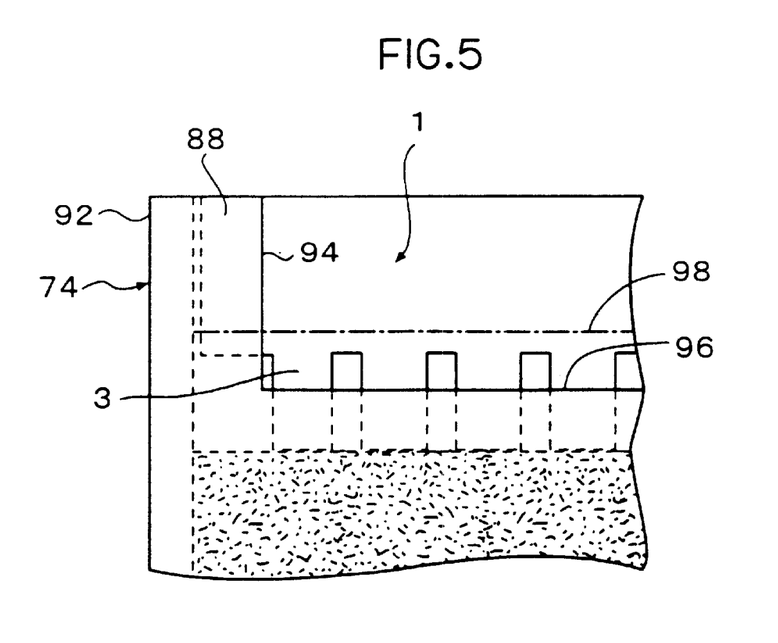
FIG. 5 is a partial enlarged plan view of the sample loading sheet of FIG. 1 as it has been inserted into the electrophoresis plate.

FIG. 5 is a front view showing partially enlarged the sample loading sheet 1 of the invention as it is set in an electrophoresis plate 74. The sample loading sheet 1 is inserted between the two glass plates, typically from above the top edge of the electrophoresis plate 74. The sample loading sheet 1 is inserted until the tips of the teeth 3 contact the upper edge of the gel electrolyte layer 90. In this way, the distance D between adjacent teeth 3 serves to separate two adjacent lanes each defined by a tooth. As shown, the top edge of the glass plate 88 which combines with the other glass plate 86 to form the electrophoresis plate is partly cut away in the longitudinal direction. If the upper buffer solution has its level 98 positioned above the bottom line 96 of the cutout 94 in the glass plate 88, it is rapidly adsorbed from the exposed surfaces (i.e., the uncoated surfaces) of the sample loading sheet 1. As a result, the DNA sample that has been adsorbed between adjacent teeth 3 of the sample loading sheet 1 is diffused by the buffer solution. If a voltage is applied to the gel electrolyte layer 90 via the upper and lower buffer solutions, the re-dissolved DNA sample migrates toward the bottom of the electrophoresis plate by flowing down the individual lanes.

Figure 6:
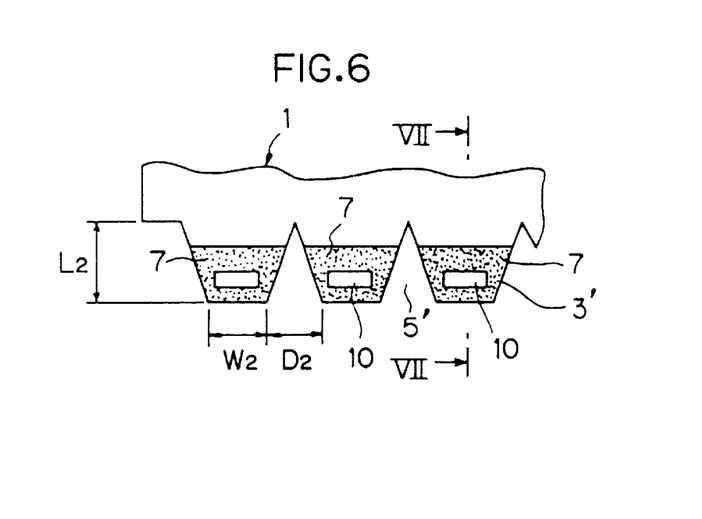
FIG. 6 is a partial enlarged plan view of another example of the sample loading sheet of the invention which has trapezoidal teeth.

FIG. 6 is a plan view showing enlarged a portion of the sample loading sheet 1 according to another embodiment of the invention. In this embodiment, each of the teeth 3' is generally of a trapezoidal shape that is tapered from the root toward the truncated tip. The length $L_2$ of each trapezoidal tooth 3' and the width $W_2$ of its truncated tip may be determined such that it has an area of about 9–24 mm² as in the case of the rectangular tooth 3 shown in FIG. 2. Adjacent trapezoidal teeth 3' are separated by a triangular cutout 5'. The values of $W_2$ and $D_2$ may be the same or either may be smaller or greater than the other. To give an example, $L_2$=5 mm, $W_2$=3 mm and $D_2$=2 mm.

Each trapezoidal tooth 3' is coated with a water-resistant or water-repellent resin film in a suitable area within the range extending from the tooth tip to the terminating end of the root. Part of the coating 7 is removed to form an opening 10 in which the cation-exchange chromatographic paper is exposed. The exposed area of the cation-exchange chromatographic paper is not particularly limited as long as it is large enough for the operator to carry out the process of injecting a DNA sample into the opening 10. The opening 10 which is shown in FIG. 6 is rectangular but it may assume any other shape such as a circle, a trapezoid or a triangle.

The method of forming the opening 10 is not particularly limited, either. If the coating 7 is formed by a printing process such as gravure printing, the opening 10 will form simultaneously. Although other methods may be used to form the opening 10, printing is the most efficient.

Figure 7:
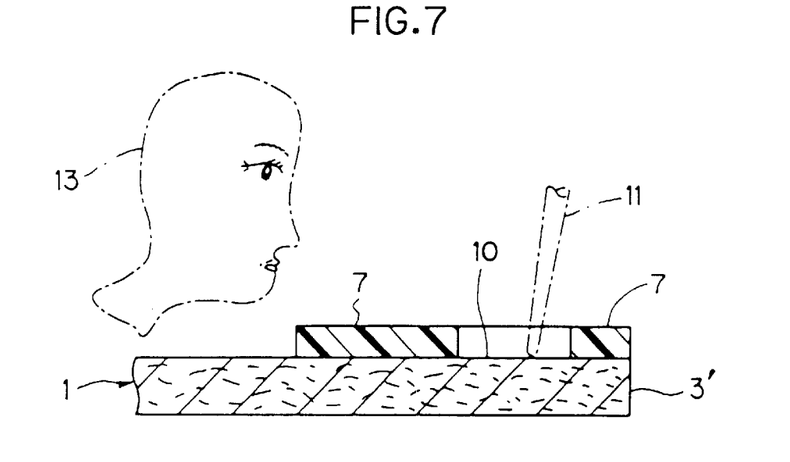
FIG. 7 is section VII—VII of FIG. 6 showing schematically how a DNA sample is adsorbed by a tooth via an opening in which the surface of cation-exchange chromatographic paper is exposed.

FIG. 7 is section VII—VII of FIG. 6. As shown, a liquid injection means 11 such as a micropipette, a micro-syringe or a capillary is pushed into the opening 10 in the coating 7 and a suitable amount of DNA sample is adsorbed by the underlying trapezoidal tooth 3' via the injection means 11. Alternatively, the trapezoidal tooth 3' may be immersed in a DNA sample solution, thereby allowing the sample to be adsorbed by the tooth 3'.

Figure 8:
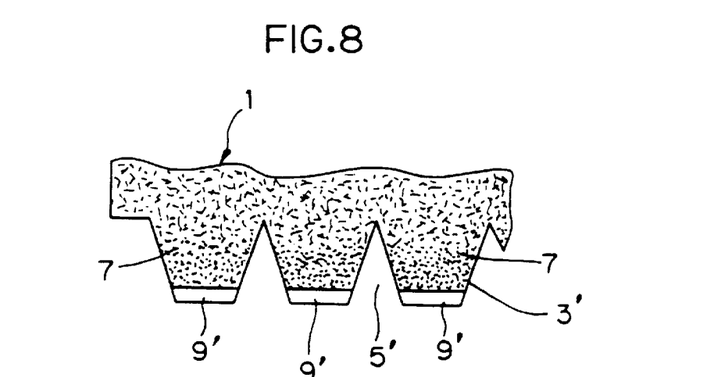
FIG. 8 is a partial enlarged plan view of yet another example of the sample loading sheet of the invention which has trapezoidal teeth.

FIG. 8 is a plan view showing diagrammatically a part of the sample loading sheet 1 according to still another embodiment of the invention. In this embodiment, one side of the sheet has the coating in the entire area except the truncated tip portions 9' of the individual trapezoidal teeth 3', where the cation-exchange chromatographic paper is exposed. The exposed tip portions 9' are not covered with a water-resistant resin film so that three sides of each tooth 3', its tip and two lateral sides, are exposed. In this embodiment, the exposed areas 9' can be formed very easily by gravure coating a water-resistant resin.

Figure 9:
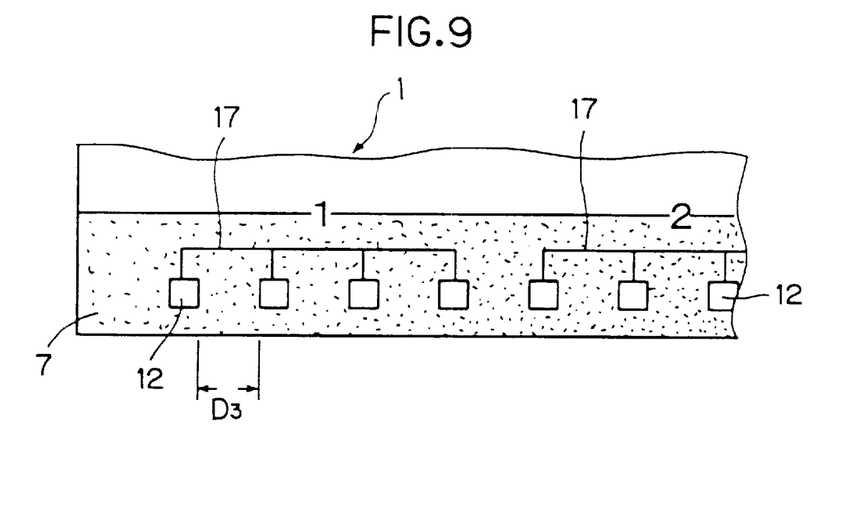
FIG. 9 is a partial enlarged plan view of still another example of the sample loading sheet of the invention which has no teeth.

FIG. 9 is a plan view showing enlarged a part of the sample loading sheet 1 according to yet another embodiment of the invention. In this embodiment, the sample loading sheet 1 has no teeth 3. The sample loading sheets 1 in the embodiments shown in FIGS. 2, 6 and 8 have separating cutouts 5 or 5' between adjacent teeth 3 or 3'. However, in the sample loading sheet 1 shown in FIG. 9, adjacent openings 12 in the coating 7 through which a DNA sample is injected are simply isolated by a distance of $D_3$. A DNA sample injected through one opening 10 is adsorbed by the cation-exchange chromatographic paper and may sometimes diffuse. In the sample loading sheets 1 in the embodiments show in FIGS. 2, 6 and 8, adjacent teeth 3 or 3' are physically isolated by the space 5 or 5' and the DNA sample injected through one tooth 3 or 3' is adsorbed by the cation-exchange chromatographic paper and may diffuse to some extent but in no case will it continue to diffuse to reach the adjacent tooth 3 or 3'. In the sample loading sheet 1 shown in FIG. 9, any two adjacent openings 12 are formed on a single continuous sheet of cation-exchange chromatographic paper and there is no space that isolates them physically. Therefore, a DNA sample injected through one opening 12 is adsorbed by the paper and may occasionally diffuse. In order to ensure that the diffusing DNA sample will not contaminate the one that has been injected through the adjacent opening 12, the distance $D_3$ between adjacent openings 12 is preferably set to be greater than the distance $D_1$ (or $D_2$) between adjacent teeth 3 (or 3') shown in FIG. 2 (or FIGS. 6 and 8). To give an example, $D_3$ is preferably within the range of 2–3 mm.

As also shown in FIG. 9, identifying means 17 may be provided on the surface of the paper to insure that the user can clearly recognize where to inject samples. Such identifying means may typically be provided by printing. For example, numerals or ruled lines may be provided to indicate sample lane groups 1–n, each group consisting of lanes for four bases A, T, C and G. Vertical ruled lines which extend upward to the top edges of the openings 12 are particularly desirable since they not only provide ease in recognizing the positions of the openings 12 but also enable the process of sample injection to be performed in an easy and rapid manner if the tip of injection means such as a micropipette is slid along a particular ruled line until it contacts the opening 7. On the other hand, horizontal ruled lines help identify the boundary between adjacent groups of sample lanes. Numerals and ruled lines may be printed in a monochromatic color such as with a black ink or different colors may be used for different groups. The lanes on either end of the sample loading sheet may be used to inject a liquid having a comparable salt concentration to the sample (the liquid may consist of a reaction buffer, a loading dye and water) in order to insure that the injected sample will be electrophoresed vertically.

Figure 10:
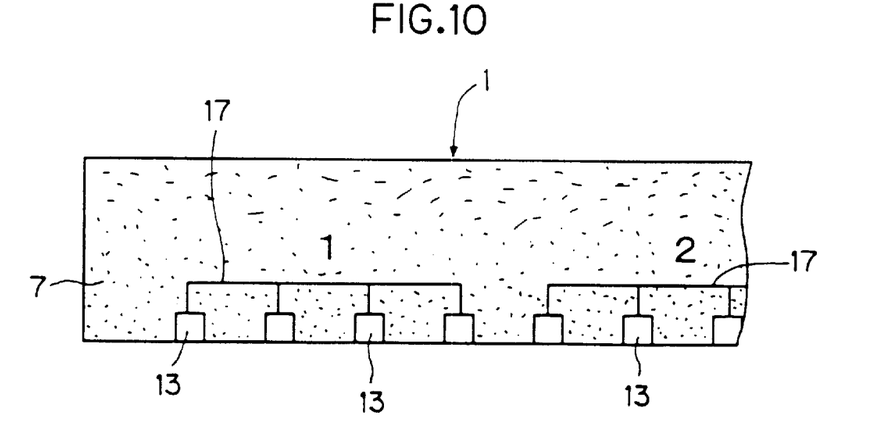
FIG. 10 is a partial enlarged plan view of a further example of the sample loading sheet of the invention which has no teeth.

FIG. 10 is a plan view showing enlarged a part of the sample loading sheet 1 according to a further embodiment of the invention. In this embodiment, openings 13 where the cation-exchange chromatographic paper is exposed are arranged along the bottom edge of the sample loading sheet 1. The sample loading sheet shown in FIG. 10 as well as the sheet shown in FIG. 9 may be provided with identifying means 17 on the surface of the cation-exchange chromatographic paper to ensure that the user can clearly recognize where to inject samples. Needless to say, the identifying means 17 for indicating where to inject samples may be provided in the sample loading sheet 1 shown in FIG. 1.

Figure 11:
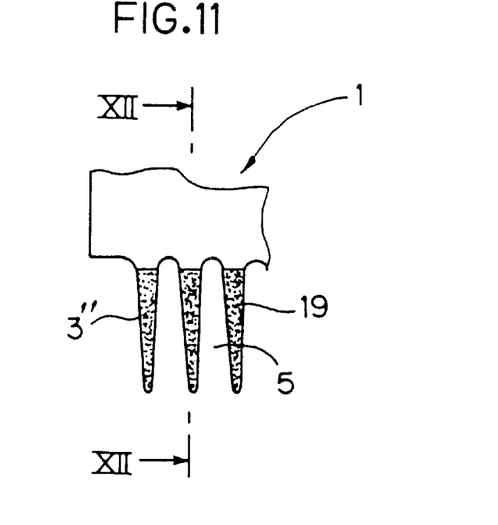
FIG. 11 is a partial enlarged plan view of yet another example of the sample loading sheet of the invention which has triangular teeth.

FIG. 11 is a plan view showing enlarged a part of the sample loading sheet 1 according to a still further embodiment of the invention. In this embodiment, the sheet 1 is made of a non-water-adsorbent material such as water-repellent or water-resistant paper or plastics. An example of the water-repellent or water-resistant paper is synthetic water-repellent or water-resistant paper and may be obtained from Oji Paper Co., Ltd. under the trade name "YUPO", which is produced from a mixture of polypropylene and an inorganic filler by biaxial drawing and filming. Polypropylene is practically nonpolar and has comparatively low stickiness. After increasing its stickiness by blending with a metal salt, a paper feedstock of polypropylene is prepared. Since anisotropy may occasionally develop during shaping into film, three polypropylene films are placed in superposition, with each having a different orientation. "YUPO" is highly water-resistant and is stronger than other types of synthetic paper. The sheet 1 shown in FIG. 11 has a plurality of triangular teeth 3" formed along either the top or bottom edge and a strip of water-adsorbing cation-exchange chromatographic paper 19 is attached to either one or the other side of each tooth 3". The strip 19 may be formed of water-adsorbing paper or a super-absorbent resin. An exemplary method of preparing the sample loading sheet 1 shown in FIG. 11 comprises the following steps: a web of non-water-adsorbing material is provided; a given width of cation-exchange chromatographic paper is attached to one longitudinal edge of the web; subsequently, the attached cation-exchange chromatographic paper is punched out to form teeth 3".

Figure 12:
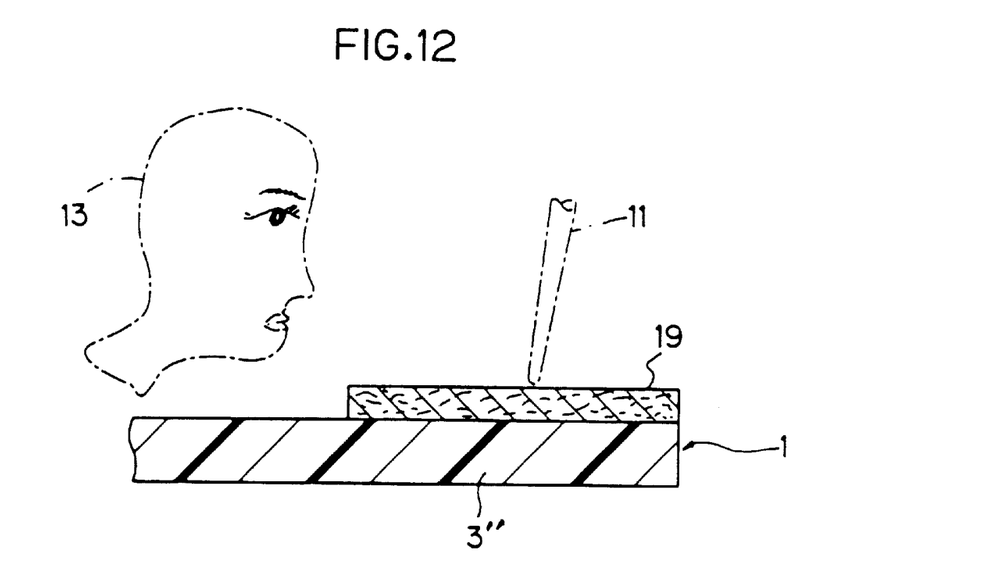
FIG. 12 is section XII—XII of FIG. 11 showing schematically how a DNA sample is adsorbed by a DNA sample absorbing portion of a tooth.

FIG. 12 is section XII—XII of FIG. 11. As shown, a liquid injection means 11 such as a micropipette, a micro-syringe or a capillary is brought close to one of the strips of cation-exchange chromatographic paper 19 on the top surfaces of the teeth 3" and a suitable amount of DNA sample is adsorbed by the paper strip 19 via the injection means 11. Alternatively, the triangular teeth 3" may be immersed directly in a DNA sample solution, thereby allowing the sample to be adsorbed by the paper strip 19 on the teeth 3".

Figure 13:
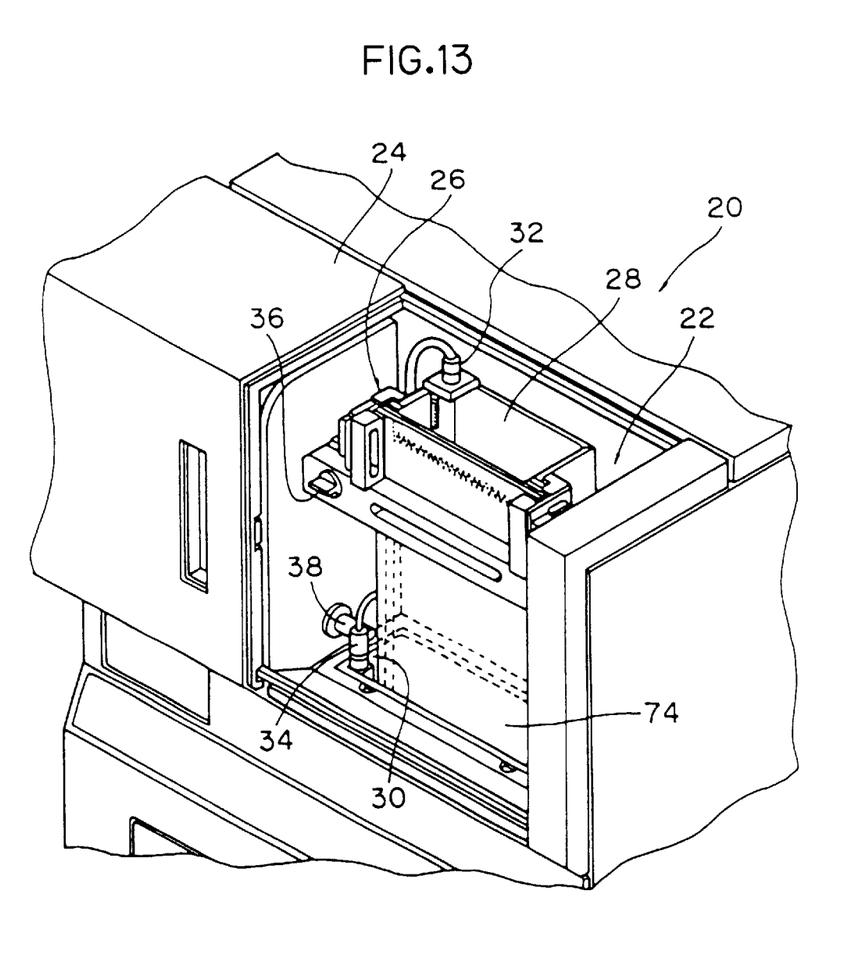
FIG. 13 is a perspective view showing diagrammatically a DNA base sequencer using the sample loading sheet of the invention.

FIG. 13 is a perspective view showing diagrammatically a DNA base sequencer using the sample loading sheet 1 of the invention. As shown, the DNA base sequencer generally indicated by 20 has an assay compartment 22 that can be shielded from light by being enclosed with a slidable cover 24 during analysis. The electrophoresis plate 74 is held vertical within the assay compartment by means of a holder 26, which also retains an upper buffer reservoir 28 in such a way that it is integral with the electrophoresis plate 74. The bottom of the electrophoresis plate 74 is placed within a lower buffer reservoir 30. When the upper buffer reservoir 28 is filled with a buffer solution, the latter flows into the electrophoresis plate 74 via the cutout in one of the two glass plates to make contact with the gel electrolyte layer. When the lower buffer reservoir 30 is filled with a buffer solution, the bottom edge of the gel electrolyte layer is immersed in the buffer solution. To ensure that a current will flow from the buffer solution in the upper reservoir through the gel electrolyte layer to the buffer solution in the lower reservoir, electrodes 32 and 34 are connected to the upper and lower buffer reservoirs, respectively. A clamp mechanism 36 is provided to allow for detachable engagement of the electrophoresis plate 74 with the holder 26. A laser light emitting end 38 is provided on a side wall of the assay compartment in such a way that the optical axis of the laser light is perpendicular to the lanes in the electrophoresis plate 74.

It should be noted that the sample loading sheet of the invention is applicable not only to the illustrated gel electrophoretic apparatus of a vertical type but also to a gel electrophoretic apparatus of a horizontal type and all other types of gel electrophoretic apparatus that use sample loading sheets. In the illustrated case, laser light is launched into the electrophoresis plate from one side; in fact, it may be applied normal to the front or back face of the electrophoresis plate or it may be incident even at an angle. The directions at which laser light is admitted into the electrophoresis plate are all known to the skilled artisan.

The effectiveness of the sample loading sheet of the invention is demonstrated below by an example.

EXAMPLE (1) Preparing Assay Samples

A 1.5-$\mu$g portion of template DNA pUC18 (consisting of 2681 bases) and 4 pmol of M13 Forward primer (with the base sequence of 5'-TGTAAAACGACGGCCAGT-3') labeled with the fluorescent dye Texas Red (trademark of Molecular Probe) were reacted in a Sanger method based sequencing reagent kit (Thermo Sequenase pre-mixed cycle sequencing kit manufactured by Amersham Pharmacia Biotech) to prepare A, C, G and T samples each having a final volume of 9 $\mu$l.

(2) Preparing an Assay Electrophoretic Gel

The electrophoretic gel reagent consisted of 6% Long Ranger (product of FMC), 6.1 mol of urea and 1.2×TBE. After adding APS and TEMED, the mixture was injected between two Pyrex plates (37 cm×20 cm×0.5 cm) held apart by a spacer 0.3 mm thick and allowed to gel. The electrophoretic buffer solutions consisted of 0.6×TBE. Preliminary electrophoresis was performed for 1 hour at an applied voltage of 1,000 V. The composition of 10×TBE was as follows: 883 mmol of Tris(hydroxymethyl)aminomethane, 886 mmol of boric acid, and 25 mmol of EDTA-2Na.

(3) Loading Samples

Webs of cation-exchange chromatographic paper P81 (invention material) and three comparisons, i.e., anion-exchange chromatographic paper (DEAE cellulose paper) DE81, conventional filter paper and glass fiber, were cut into shapes and subsequently processed to prepare sample loading sheets each having rectangular teeth as shown in FIGS. 1 and 3C. The fluorescence-labeled DNA samples prepared in (1) were pipetted, in the order of bases A, C, G and T, in 1.5-$\mu$l portions at the tips of the teeth of each sample loading sheet so that they were adsorbed by the individual teeth. Each of the sample loading sheets was then inserted into the top of a gel electrolyte layer in an electrophoresis plate as shown in FIG. 5. As a control, a paper sharktooth comb of the type shown in FIG. 16 was inserted into the electrophoresis plate until it was slightly buried in the top of the gel electrolyte layer as shown in FIG. 17; thereafter, the fluorescence-labeled DNA samples prepared in (1) were injected, in the order of bases A, C, G and T, in 1.5-$\mu$l portions with a polycarbonate capillary at a site which is indicated by 121 in FIG. 17 and under the space 115 between adjacent teeth.

(4) Electrophoresis and Fluorescence Detection

Each of the electrophoresis plates loaded with samples in (3) was set in a DNA base sequencer commercially available from Hitachi Electronics Engineering Co., Ltd. under the trade name "SQ5500". After applying a voltage of 1,400 volts for 2 minutes to the electrophoresis plates, the control (paper-made sharktooth comb) and the sample loading sheets made of P81, DE81, filter paper and glass fiber were removed from the electrophoresis plates and electrophoresis was carried out at a voltage of 1,400 volts for 10 hours. Each sample migrated a distance of 27.5 cm from the loading position to the point where it was illuminated with HeNe laser light and subjected to fluorescence detection.

(5) Results of Measurements

Figure 19:
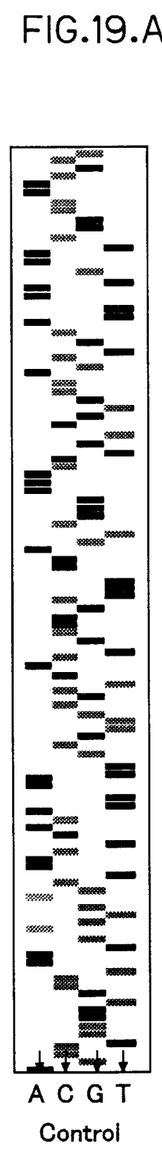
FIGS. 19A, 19B, 19C, 19D and 19E show ladder patterns obtained in various electrophoretic runs that were performed in the Example.

FIG. 19A shows the ladder patterns from the control. From these ladder patterns, the base sequence of the fluorescence-labeled DNA samples under assay was determined and used as a control reference.

FIG. 19B shows the ladder patterns from the sample loading sheet made of cation-exchange chromatographic paper P81 (invention material). Obviously, the resolution of the ladder patterns shown in FIG. 19B is almost comparable to that of the control ladder patterns. Sequencing based on these ladder patterns revealed a base sequence completely identical to that determined for the control.

FIG. 19C shows the ladder patterns from the sample loading sheet made of anion-exchange chromatographic paper DE81. Obviously, the fluorescence-labeled DNA samples did not migrate at all. This is probably because the fluorescence-labeled DNA samples were adsorbed on DE81 so strongly that they could not detach from it upon immersion in the buffer solution and subsequent application of high voltage.

FIG. 19D shows the ladder patterns from the sample loading sheet made of conventional filter paper. Obviously, the fluorescence-labeled DNA samples caused "tailing" and could not be separated at high resolution. Given such a low resolution, it was extremely difficult to determine the base sequence of the samples. The reason for this low resolution may be explained as follows: due to the strong adsorption on the conventional filter paper, the fluorescence-labeled DNA samples could only be detached in small amounts from the filter paper even when the sample loading sheet was immersed in the buffer solution and subsequently placed in a high-voltage field.

FIG. 19E shows the ladder patterns from the sample loading sheet made of glass fiber. Obviously, the sample loading sheet made of glass fiber has an even lower resolution than the one made of the conventional filter paper. This result may be attributable to the adsorption on glass fiber which is higher than that on the conventional filter paper. With this low resolution, the sample loading sheet made of glass fiber is by no means suitable for practical use in assay.

As described on the foregoing pages, the sample loading sheet of the invention for use on a DNA base sequencer is made of cation-exchange chromatographic paper and is capable of positive adsorption of DNA samples. A DNA sample adsorbed by the loading sheet of the invention migrates to give ladder patterns at a high resolution which is almost comparable to the resolution achieved by directly loading the sample onto a gel electrolyte layer in the prior art. The sample loading sheet of the invention enables DNA samples to be injected in a very easy and efficient manner. For instance, using the sample loading sheet of the invention, DNA samples can be injected quite easily in a different place than where the loading sheet is subsequently inserted into an electrophoresis plate. Since the time required by sample loading is considerably reduced, the overall operating time for DNA base sequencing is sufficiently shortened to achieve a marked improvement in the throughput of analysis.

2. The sample loading sheet according to claim 1, wherein the cation-exchange chromatographic paper is a cation-exchange cellulose phosphate paper.

3. The sample loading sheet according to claim 1, which has a plurality of rectangular teeth formed on either the top or bottom edge thereof, with adjacent teeth being isolated by a space, at least a portion of the flat area of each of said teeth being coated with a water-resistant resin film.

4. The sample loading sheet according to claim 1, which has a plurality of trapezoidal teeth formed on either the top or bottom edge thereof through which the assay sample is to be loaded into the gel electrolyte layer, with adjacent teeth being isolated by a space, each of said teeth being tapered from the root toward the tip and coated with a water-resistant film on at least a portion of the area of the major surface of the cation-exchange chromatographic paper extending from the tooth tip to the root, an opening being present in the applied coating through which the surface of said cation-exchange chromatographic paper is exposed, and said opening being sufficient to provide access for receiving a liquid assay sample therethrough.

5. The sample loading sheet according to claim 1, wherein a plurality of openings are present in part of the applied coating along either the top or bottom edge and a nearby area through which the surface of said cation-exchange chromatographic paper is exposed, and said openings being sufficient to provide access for receiving a liquid assay sample therethrough.

6. A sample loading sheet for loading an assay sample via specified lanes into a gel electrolyte layer in an electrophoresis plate to be used in a gel electrophoretic apparatus, said sheet being formed of a non-water-adsorbing material and having a plurality of teeth formed on either the top or bottom edge thereof, with adjacent teeth being isolated by a space,

What is claimed is:

1. A sample loading sheet for loading an assay sample via specified lanes into a gel electrolyte layer in an electrophoresis plate to be used in a gel electrophoretic apparatus, said sheet being formed of cation-exchange chromatographic paper and having part or all of at least one principal surface thereof coated with a water-resistant resin film, said cation-exchange chromatographic paper embodying teeth that correspond to said specified lanes, and a liquid assay sample being absorbed by said teeth.

a strip of cation-exchange chromatographic paper that is adsorbent with respect to a liquid assay sample being attached to at least a portion of the area extending from the tooth tip to the root, and said cation-exchange chromatographic paper embodying said specified lanes.

7. The sample loading sheet according to claim 6, which is formed of water-repellent or water-resistant paper or plastics, wherein said strip of cation-exchange chromatographic paper is a cation-exchange cellulose phosphate paper.

* * * * *

SEQUENCE LISTING

<160> NUMBER OF SEQ ID NOS: 1

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 1
tgtaaaacga cggccagt                                                    18